(12) United States Patent
Claesson

(10) Patent No.: US 8,798,234 B2
(45) Date of Patent: Aug. 5, 2014

(54) IMAGING DURING RADIOTHERAPY

(75) Inventor: Åke Claesson, Uppsala (SE)

(73) Assignee: Elekta AB (Publ), Stockholm (SE)

( * ) Notice: Subject to any disclaimer, the term of this patent is extended or adjusted under 35 U.S.C. 154(b) by 208 days.

(21) Appl. No.: 13/435,128

(22) Filed: Mar. 30, 2012

(65) Prior Publication Data

US 2013/0256565 A1 Oct. 3, 2013

(51) Int. Cl.
*A61N 5/10* (2006.01)
*A61B 6/03* (2006.01)

(52) U.S. Cl.
USPC .......... 378/65; 378/5; 378/9; 378/37; 378/41; 378/68; 600/427; 250/492.1

(58) Field of Classification Search
USPC .................. 600/407, 414, 427, 431; 382/132; 378/5, 37, 41, 65
See application file for complete search history.

(56) References Cited

U.S. PATENT DOCUMENTS

| | | | |
|---|---|---|---|
| 7,076,023 B2 * | 7/2006 | Ghelmansarai et al. | 378/65 |
| 7,945,021 B2 * | 5/2011 | Shapiro et al. | 378/65 |
| 2008/0183070 A1 * | 7/2008 | Unal et al. | 600/414 |
| 2009/0238334 A1 * | 9/2009 | Brahme et al. | 378/41 |
| 2010/0074400 A1 * | 3/2010 | Sendai | 378/37 |
| 2011/0089042 A1 | 4/2011 | De Oliveira et al. | 205/223 |
| 2012/0008735 A1 * | 1/2012 | Maurer et al. | 378/5 |
| 2012/0035470 A1 * | 2/2012 | Kuduvalli et al. | 600/427 |
| 2013/0060134 A1 * | 3/2013 | Eshima et al. | 600/431 |
| 2013/0188856 A1 * | 7/2013 | Adler et al. | 382/132 |

FOREIGN PATENT DOCUMENTS

| | | | | |
|---|---|---|---|---|
| WO | WO 99/21211 | 4/1999 | | H01J 47/00 |
| WO | WO 2005/006017 | 1/2005 | | G01T 1/29 |

* cited by examiner

*Primary Examiner* — Baisakhi Roy
(74) *Attorney, Agent, or Firm* — Sunstein Kann Murphy & Timbers LLP

(57) ABSTRACT

We provide a radiotherapy apparatus including a source of therapeutic radiation, a source of imaging radiation having an energy level less than that of the therapeutic radiation, a detector for radiation lying within the field of both the therapeutic radiation and the imaging radiation and able to image both, a first imaging circuit supplied with the output of the detector, a second imaging circuit also supplied with the output of the detector, a first pulse trigger circuit adapted to trigger the source of therapeutic radiation to produce a pulse of therapeutic radiation and to trigger the first imaging circuit to capture an output of the detector; and a second pulse trigger circuit adapted to trigger the source of imaging radiation to produce a pulse of imaging radiation and to trigger the second imaging circuit to capture an output of the detector.

13 Claims, 2 Drawing Sheets

IMAGING DURING RADIOTHERAPY

FIELD OF THE INVENTION

The present invention relates to methods of (and apparatus for) imaging a patient during a radiotherapy treatment.

BACKGROUND ART

Radiotherapy is often carried out by directing a high-energy beam of x-rays, typically at an energy level of several MeV, towards a tumour within a patient. This beam damages tissue that it passes through, tumour tissue more so than healthy tissue, so is collimated to reduce the amount of healthy tissue that is exposed to the beam. It is also directed towards the patient from a number of different directions, each passing through the tumour or other target point, so that any particular section of healthy tissue only receives a fraction of the total dose delivered during that treatment session (or "fraction"). This can be done by mounting the beam source on a gantry that is rotatable around the patient, thereby allowing it to be delivered from any chosen angle. Usually, the patient will be supported so that the tumour lies at the meeting-point of the rotation axis and the central axis of the beam, a location known as the "isocentre".

This so-called MV beam can also be used for imaging the patient. However, the contrast between different tissue types at this energy level is poor, and the beam will also be collimated in order to limit the dosage to the patient. For this reason, a lower-energy beam is typically used for imaging purposes, having an energy of several keV at which the contrast between tissue types is more marked. So-called KV beams are often provided on radiotherapeutic apparatus for carrying out diagnostic imaging prior to and during radiotherapy.

It is known to image a patient during radiotherapy treatment using both the therapeutic (MV) beam and a diagnostic (kV) beam. This allows an operator to control and review the therapy in real time, confirming that the therapeutic beam is directed and collimated correctly with respect to the patient and that the patient is in the correct position.

However, this normally requires two separate imaging systems, one for the MV beam and one for the kV beam. Efforts to combine kV and MV imaging on the same detector have suffered from a perceived need to switch off the MV beam completely during kV imaging so that it does not spoil the kV image. Two detectors are therefore provided. Often, these are located on the rotatable gantry that supports the radiation head in positions that are 90° apart, allowing both to operate in parallel and largely independently, absent issues such as scattering. This imposes a significant material cost, however.

SUMMARY OF THE INVENTION

It would be beneficial to be able to use the same detection systems for both the MV and kV beams. This would give the two beams the same or a closely-similar viewpoint and would reduce the material cost of the system. However, the switchover period between the two systems is significant, and the waiting time this would impose would therefore result in delay during treatment. The markedly different dose rate between the two types of beams means that it is not possible to collect them simultaneously.

The present invention therefore provides a radiotherapy apparatus, comprising a source of therapeutic radiation, a source of imaging radiation having an energy level less than that of the therapeutic radiation, a detector for radiation, lying within the field of both the therapeutic radiation and the imaging radiation and able to image both, a first imaging circuit supplied with the output of the detector, a second imaging circuit also supplied with the output of the detector, a first pulse trigger circuit, adapted to trigger the source of therapeutic radiation to produce a pulse of therapeutic radiation, and to trigger the first imaging circuit to capture an output of the detector; and a second pulse trigger circuit, adapted to trigger the source of imaging radiation to produce a pulse of imaging radiation, and to trigger the second imaging circuit to capture an output of the detector. This permits the two imaging circuits to retain settings (such as amplification, lateral translation and the like) that are individual to either the therapeutic radiation or the diagnostic radiation. As a result, there is no delay time while a single image capture circuit recalibrates for the different radiation.

The first & second imaging circuits will usually each include at least one signal amplifier acting on the output of the detector to normalise the output to a predetermined level. Indeed, they could be separate channels of a multi-mode amplifier. The output of both the first and second imaging circuits can be fed to a common display to allow an operator to view both.

The detector is preferably a two-dimensional flat-panel detector, allowing a view to be provided online for the operator and to be used for CT purposes. We have found that a detector based on the gas-electron-multiplier principle set out in WO99/21211 has a very short "after-burn" time constant, thus allowing a KV image to be captured very soon after an MV pulse.

In a further aspect of the present invention, a radiotherapy apparatus is provided comprising a source of therapeutic radiation, a source of imaging radiation having an energy level less than that of the therapeutic radiation, a detector for radiation lying within the field of both the therapeutic radiation and the imaging radiation and comprising a gas-electron multiplier, and a control means arranged to trigger the source of therapeutic radiation to emit pulses of therapeutic radiation on a pulsed basis with a duty cycle of less than one half, trigger the source of imaging radiation to emit pulses of imaging radiation between pulses of the therapeutic radiation, and to trigger the detector to capture an image of at least the imaging radiation. This allows the apparatus to capture diagnostic-quality images in real time simultaneously with delivery of therapeutic radiation, without needing to delay or prolong the treatment.

In this aspect, the detector can also capture images from the therapeutic radiation, if desired.

The therapeutic radiation typically has an energy of at least 1 MeV, and the therapeutic radiation typically has an energy of at least 1 keV.

BRIEF DESCRIPTION OF THE DRAWINGS

An embodiment of the present invention will now be described by way of example, with reference to the accompanying figures in which.

DETAILED DESCRIPTION OF THE EMBODIMENTS

An MV beam for use in radiation therapy is typically delivered in pulses lasting 3-5 us, with a pulse repetition frequency ("PRF") between 100-500 Hz. Accordingly, there is plenty of time (between 2 and 10 ms) to send a kV pulse of imaging radiation in between the MV pulses. By using a fast detector with a very short afterburn time (i.e. the time required for the effects of the MV pulse to dissipate), one can send one or more kV pulses between each MV pulse. This will allow the kV and MV pulses to be read and processed with the same detector, and still kept them separate from each other throughout the image processing.

A suitable detector meeting these requirements is a GEM-type detector ("Gas Electron Multiplier"). Such detectors are disclosed in WO99/21211, the content of which is hereby incorporated by reference and to which the skilled reader is directed for a complete understanding of the present invention. GEM detectors comprise a pair of plates separated by a suitable gas and across which a large potential is applied. Ionising radiation that passes through the detector creates one or more free electrons in the gas, which are accelerated by the electric field resulting from the potential difference. Between the two end plates, there is a multiplier plate which is largely insulating but has conductive top and bottom faces, across which there is also a large potential difference. The multiplier plate also has a series of through-holes. The result is that electrons travelling through the detector are directed through the holes in the multiplier plate and concentrated. This, together with the electric field created by the multiplier plate, causes an electron cascade to be created which multiples the number of electrons and magnifies the signal.

The GEM detector was developed in order to allow for greater sensitivity to small signals, and to have a longer life expectancy under exposure to high levels of ionising radiation. However, we have noted that it also has a very short afterburn time and is thus available to detect a kV pulse very quickly after an MV pulse passes through. Other detectors that are suitable include certain types of diode array, etc.

Figure 1:
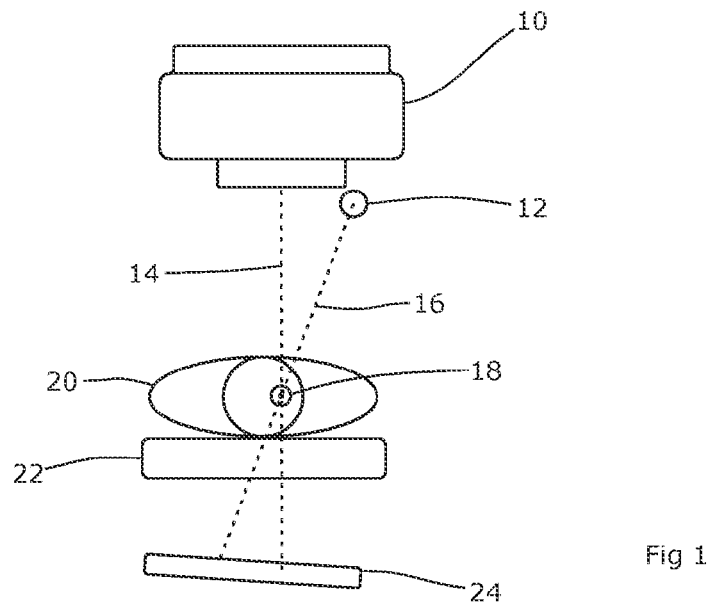
FIG. 1 shows a schematic layout of the apparatus.

Referring to FIG. 1, the apparatus of the present invention thus has an MV therapeutic source 10 and a kV diagnostic source 12, supported on a main gantry arm (not shown). These emit, respectively, an MV beam 14 and a kV beam 16 which are both directed towards a common isocentre 18. A patient 20 is supported on a patient table 22 so that they are appropriately located relative to the isocentre 18. A single detector 24 is supported on a secondary gantry arm (not shown) in the path of both beams, on the opposite side of the patient 20 so as to image the beams after attenuation by the patient 20.

As illustrated, the MV source 10 and the kV source 12 are separate. They can alternatively be combined into a single source which will have the advantage of allowing a common point of view for both beams.

Figure 2:
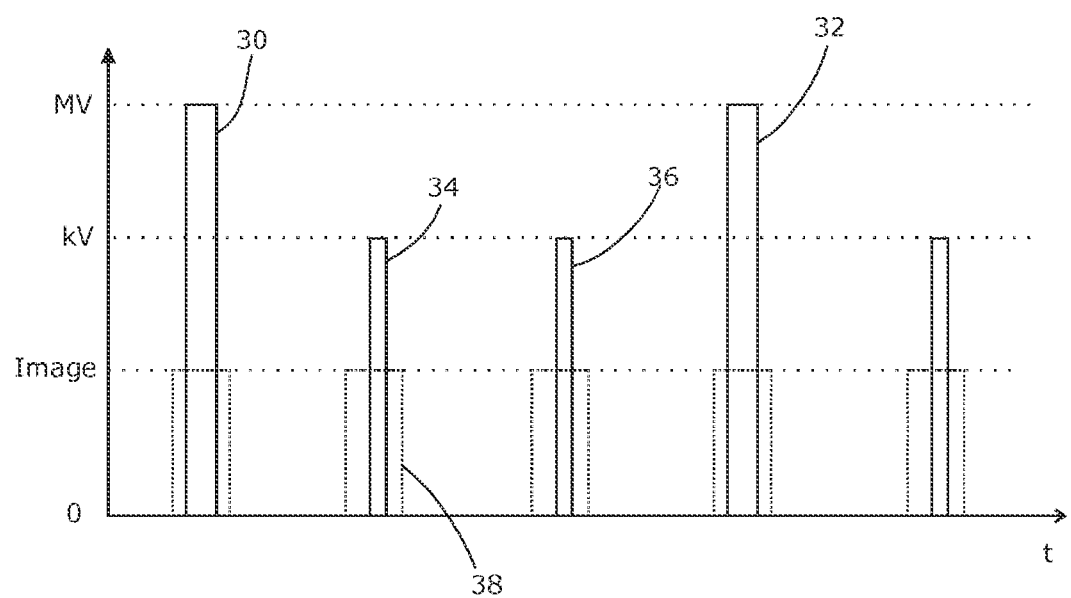
FIG. 2 shows a timing diagram for the invention.

FIG. 2 shows a timing diagram for the apparatus of FIG. 1. MV pulses 30, 32 of approximately 3-5 µs width and 400 Hz frequency are issued by the MV source 10. For clarity, the pulses are shown wider than would be the case if they were to scale; if to scale then the pulses would be $\frac{1}{500}^{th}$ of the space between them. There is thus adequate time to send a pair of kV pulses 34, 36, evenly spaced between the MV pulses 30, 32.

The imaging system 24 is activated at a 1200 Hz frequency 38 and thus catches both the MV pulses 30, 32 and the kV pulses 34, 36. By switching the image data collection and handling system between kV and MV modes respectively, kV and MV images can be processed. Different settings for amplification etc. will usually need to be applied in order to achieve optimal image quality for the kV and MV images respectively, as the very different beam properties mean that the signals received from the detector will differ as to their tonal qualities, etc. In other words, by being able to keep kV and MV images separated in time, kV image quality will not be compromised by the MV imaging system, and vice versa.

One or several imaging kV pulses are shot and images captured between therapy beam MV pulses. kV and MV images are captured by switching on the detector when a MV or kV pulse is expected. Once the image is captured, the detector is switched off until the next pulse is expected. The detector read-out system should be triggered by the MV beam PRF and the kV imaging PRFs respectively. The duration of the image capturing cycle, or sample time, depends on the response-time and quantum efficiency etc. of the detector. With a sensitive and fast detector, the sample time could be made shorter than the kV or MV pulse, something that would possibly reduce or eliminate possible energy-spread effects caused by time-response function of the MV and kV beam generators, respectively.

Figure 3:
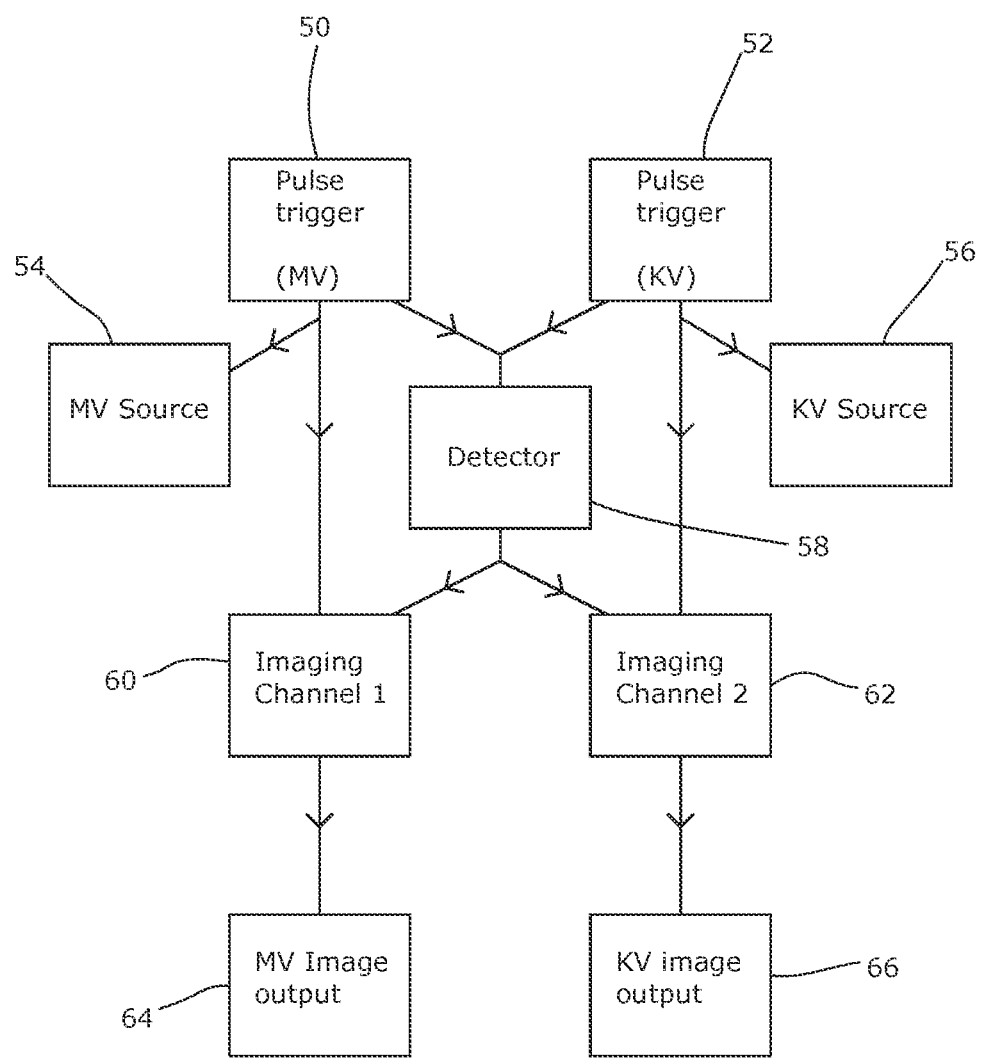
FIG. 3 shows a logical layout of the control systems.

FIG. 3 shows a logical layout of the control system. Separate pulse triggers are provided for the MV system 50 and the kV system 52. The MV trigger 50 is fed to the MV source 54 to produce MV pulses according to the timing diagram shown in FIG. 2, and likewise the kV trigger 52 is fed to the kV source 56.

Both trigger signals 50, 52 are also routed to the detector 58 so that it is active when a pulse is to be issued. The output of the detector 58 is fed to two separate imaging channels, a first channel 60 and a second channel 62. The first channel 60 also receives the MV pulse trigger 50, and is thus activated when the detector 58 is imaging an MV pulse but not when the detector 58 is imaging an kV pulse. Conversely, the second channel 62 receives the kV pulse trigger 52, and is thus activated when the detector 58 is imaging a kV pulse but not when the detector 58 is imaging an MV pulse. Each imaging channel can thus be configured with the necessary amplification, contrast, offset (etc) settings required for the image type that it is receiving, and no delay is therefore imposed by the time needed to re-set the imaging channel(s) accordingly.

Each imaging channel 60, 62 then feeds its output to a respective image output 64, 66. This can then be displayed, analysed, stored, combined, or otherwise handled as desired.

It will of course be understood that many variations may be made to the above-described embodiment without departing from the scope of the present invention.

The invention claimed is:

1. Radiotherapy apparatus comprising;
   a source of therapeutic radiation,
   a source of imaging radiation having an energy level less than that of the therapeutic radiation,
   a detector for radiation, lying within the field of both the therapeutic radiation and the imaging radiation and able to image both,
   a first imaging circuit supplied with the output of the detector,
   a second imaging circuit also supplied with the output of the detector,
   a first pulse trigger circuit, adapted to trigger the source of therapeutic radiation to produce a pulse of therapeutic radiation, and to trigger the first imaging circuit to capture an output of the detector; and
   a second pulse trigger circuit, adapted to trigger the source of imaging radiation to produce a pulse of imaging radiation, and to trigger the second imaging circuit to capture an output of the detector.

2. Radiotherapy apparatus according to claim 1 in which the detector is a two-dimensional flat-panel detector.

3. Radiotherapy apparatus according to claim 1 in which the detector is a gas-electron-multiplier.

4. Radiotherapy apparatus according to claim 1 in which the first & second imaging circuits each include at least one signal amplifier acting on the output of the detector to normalise the output to a predetermined level.

5. Radiotherapy apparatus according to claim 1 in which the output of both the first and second imaging circuits is fed to a common display.

6. Radiotherapy apparatus according to claim 1 in which the first imaging circuit and the second imaging circuit are separate channels of a multi-mode amplifier.

7. Radiotherapy apparatus according to claim 1 in which the therapeutic radiation has an energy of at least 1 MeV.

8. Radiotherapy apparatus according to claim 1 in which the therapeutic radiation has an energy of at least 1 keV.

9. Radiotherapy apparatus comprising:
   a source of therapeutic radiation,
   a source of imaging radiation having an energy level less than that of the therapeutic radiation,
   a detector for radiation lying within the field of both the therapeutic radiation and the imaging radiation and comprising a gas-electron multiplier, and
   a control means arranged to:
   i. trigger the source of therapeutic radiation to emit pulses of therapeutic radiation on a pulsed basis with a duty cycle of less than one half,
   ii. trigger the source of imaging radiation to emit pulses of imaging radiation between pulses of the therapeutic radiation, and
   iii. trigger the detector to capture an image of at least the imaging radiation.

10. Radiotherapy apparatus according to claim 9 in which the control means is further arranged to trigger the detector to capture an image of the therapeutic radiation.

11. Radiotherapy apparatus according to claim 9 in which the first imaging circuit and the second imaging circuit are separate channels of a multi-mode amplifier.

12. Radiotherapy apparatus according to claim 9 in which the therapeutic radiation has an energy of at least 1 MeV.

13. Radiotherapy apparatus according to claim 9 in which the therapeutic radiation has an energy of at least 1 keV.

* * * * *